United States Patent [19]

Andermann et al.

[11] Patent Number: 4,837,021

[45] Date of Patent: Jun. 6, 1989

[54] TWO PART TISSUE IRRIGATING SOLUTION

[75] Inventors: Guy Andermann, Colmar; Georges de Burlet, Kaysersberg; Michel Dietz, Kaysersberg; Joseph Spittler, Kaysersberg, all of France

[73] Assignee: Laboratoires P.O.S., Kaysersberg, France

[21] Appl. No.: 948,188

[22] Filed: Dec. 31, 1986

[51] Int. Cl.$^4$ .................... A61K 33/00; A61K 33/42; A61K 33/14; A61K 33/06
[52] U.S. Cl. ........................... 424/602; 514/912; 424/605; 424/677; 424/681; 424/717
[58] Field of Search .............. 424/127, 128, 153, 154, 424/156

[56] References Cited

U.S. PATENT DOCUMENTS 4,443,432 4/1984 Garabedian et al. .............. 424/127
4,550,022 10/1985 Garabedian et al. .............. 424/127

OTHER PUBLICATIONS

Vidal et al., "GABA Influences Rabbit Corneal Deturgescence" *Chem Abst.* 93:231294k, p. 106 (1980).
Dikstein, et al. "Corneal Endothelial Pumping in the Presence of Insulin and GABA", *Exp. Eye Res.*, 31, 239–241 (1980).

*Primary Examiner*—Douglas W. Robinson
*Assistant Examiner*—Raymond J. Henley, III
*Attorney, Agent, or Firm*—James A. Arno; Gregg C. Brown

[57] ABSTRACT

A tissue irrigating solution useful for irrigating animal tissue, such as ocular tissue and neuro tissue, during surgery, contains sodium, potassium, magnesium calcium chloride, and bicarbonate ions as well as dextrose, glutathione, and gamma-amino butyric acid (GABA) or functional analogue(s) of GABA, or a mixture of GABA and such analogue(s) in proportions consistent with the osmotic stability and continued metabolism of the tissue cells. The irrigating solution is prepared by mixing a first basic solution which provides the bicarbonate and a second acidic solution which provides the calcium, magnesium, dextrose and glutathione. The first and second solutions may be stored as stable, sterile solutions for extended periods of time and mixed within 24 hours of use.

16 Claims, No Drawings

TWO PART TISSUE IRRIGATING SOLUTION

BACKGROUND OF THE INVENTION

This invention relates to electrolyte solutions for use within the human body and more particularly to solutions useful for irrigating tissues during surgery, particularly eye surgery.

This invention also, and specifically relates to ophthalmic irrigating solutions which comprise, in addition to conventional components, an effective amount of gamma-amino butyric acid (GABA) or functionally equivalent analogues thereof, such as, diamino butyric acid (DABA), and mixtures thereof. Agents, such as, GABA, are known to facilitate deturgescence of the cornea via maintenance of the corneal endothelial fluid pump (Dikstein, et al., *Exp. Eye Res.*, 1980, 31, 239–241). Without such deturgescence the cornea would swell and lose clarity. Reference to conventional irrigating solutions, or at least to conventional components thereof, is further made a part of the present disclosure by the incorporation by reference of U.S. Pat. No. 4,550,220, which discloses such irrigating solutions.

Any scission into the human body is detrimental to the human body and invariably results in cell loss. The need to keep cell loss to a minimum is particularly crucial during any surgical procedure performed on delicate and irreplaceable tissues, such as the tissues of the eye, nerves, etc.

The cornea of the eye is comprised of five layers: epithelium, Bowman's membrane, stroma, Decemet's membrane, and endothelium. The endothelium layer is particularly vulnerable to trauma as the endothelial cells are infrequently, if ever, replaced as a normal process in the adult life. The endothelium is principally responsible for the maintenance of the proper state of hydration of the stromal layer. The stromal layer has a tendency to imbibe fluid, a tendency which is counterbalanced by outward fluid transport via the endothelium. If the proper fluid balance is not maintained in the stromal layer, the cornea thickens and the characteristic transparency of the cornea is lost. Accordingly, cell loss or damage in the endothelial layer will result in decreased vision. Failure of the endothelium to perform its fluid transport function for short periods of time will result in corneal thickening and visual clouding. Because of the importance of, and the vulnerability of, the endothelial layer, it is necessary during eye surgery, such as cataract and retinal surgery or corneal transplants, to make provisions for the protection of the endothelial cells.

A significant factor causing cell loss during tissue scission is the traumatic change in environment experienced by the internal cells. Exposure to the atmosphere presents a far different environment for the cells than is provided by the natural fluids in which they are bathed. To simulate the natural cellular environment and thereby prevent cell damage, exposed tissue during surgery is frequently irrigated in solutions which attempt to approximate natural body fluids. The value of bathing eye tissue during surgery to prevent cell damage has long been recognized. For internal ocular tissues, such as the endothelium, the aqueous humor is the natural bathing fluid and, hence, an ophthalmic irrigating solution to protect the endothelium should as closely as possible resemble the aqueous humor.

Of primary concern in a tissue irrigating solution is that the osmolality of the solution be generally isotonic with cellular fluids so as to maintain equal osmotic pressure within and without the cell membranes. To this end, one of the early ophthalmic irrigating solutions was isotonic (0.9%) saline. However, as has long been recognized, isotonic saline is quite inadequate as an opthalmic irrigating solution and has been shown to result in endothelial cell swelling, cell damage, and consequent corneal clouding.

Because of the inadequacy of isotonic saline, various alternative electrolyte solutions have been proposed as ophthalmic irrigating solutions in attempts to provide solutions which more closely resemble the aqueous humor and prevent cell damage and corneal clouding. Standard electrolyte solutions primarily intended for injection solutions, such as Ringer's solution and lactated Ringer's solution, have been used as ophthalmic irrigating solutions because of their wide availability as sterile solutions.

A solution intended for ophthalmic irrigation known as balanced salt solution (BSS) has also been developed. BSS contains the essential ions, calcium, sodium, potassium, magnesium and chloride in generally optimal concentrations for ocular tissue, and has an acetate-citrate buffer system which is compatible with divalent calcium and magnesium ions.

The various electrolyte solutions used for ophthalmic irrigation have been improvements over normal saline by providing necessary ions in addition to $Na^+$ and $Cl^-$ as provided by isotonic saline. $Mg^{++}$ is an important cofactor for adenosine triphosphatase, an enzyme which plays an important role in mediating the fluid transport pump in the eye. $Ca^{++}$ is necessary to maintain the endothelial junction. $K^+$ is an important factor in many biochemical processes, and the fluid transport pump of the endothelium requires a proper $Na^+/K^+$ ratio. The previously known electrolyte solutions used to irrigate ocular tissue have reduced but not eliminated corneal swelling and cell damage.

The need for improved ophthalmic irrigating solutions continues, particularly in view of new surgical techniques which may probe deeper into the eye and require several hours of operating time. Surgical advances now permit surgery in the vitreous (posterior) chamber to remove opacified vitreous humor or to repair retinal detachment. Such operations require significant time, e.g., 1 to 3 hours, and large volumes of irrigating solution, e.g., 100–1000 ml.

During eye surgery and particularly during surgery which requires extended periods of time, proper electrolytic balance alone is insufficient to retain normal corneal thickness. To maintain proper corneal thickness and prevent cell damage, an irrigating solution in addition to electrolytic balance must provide metabolic support and must particularly provide factors needed for the enzyme-mediated $Na^+/K^+$ pump system through which excess fluid is removed from the stroma.

To incorporate factors necessary for sustained metabolism by endothelial cells, glutathione-bicarbonate-Ringers solution (GBR) was developed in which $NaHCO_3$, glutathione, dextrose and adenosine (an optional ingredient) are added to Ringer's solution. Bicarbonate, dextrose and glutathione have been shown to be important factors in maintaining structural integrity of endothelial cells. The aqueous humor has a bicarbonate buffer system. Dextrose (d-glucose) provides a substrate for various metabolic pathways, and glutathione has been shown to aid the metabolic pump mechanism by maintaining proper Na+/K+ adenosine-triphosphatase. GBR has been shown effective in maintaining corneal thickness and endothelial cell integrity for up to three hours.

While the effectiveness of a GBR ocular irrigating solution has been shown both in vivo and in vitro, its use in surgery has been limited for reasons of stability and sterility. It is to be appreciated that sterility of an ophthalmic irrigating solution is absolutely essential. To insure sterility, it is desirable that an irrigating solution be prepackaged so that the quality and sterility may be closely monitored and tested as contrasted with an extemporaneously mixed solution as might be prepared in a hospital pharmacy. The solution will perfuse the eye in essentially a closed system where even a small number of organisms could produce an overwhelming endophthalmitis, as pseudomonas is one of the very few organisms that has very few metabolic requirements and can grow with a minimal nutrient supply such as phosphate and bicarbonate. Dr. Jan Worst has reported on a series of infections in Europe with pseudomonas-contaminated irrigating solutions. (January 1978, *American Intraocular Implant Society Journal*).

GBR may not be prepackaged due to the long term incompatability and/or instability of its various moieties. Of the moieties added to Ringer's solution to formulate GBR, bicarbonate is perhaps the most important (McEnerney et al. *Investigative Ophthamology and Visual Science* 16 No. 7, July 1977). Unfortunately the bicarbonate as well as the phosphate in a bicarbonate-phosphate buffer system form insoluble precipitates with $Mg^{++}$ and $Ca^{++}$. While at the ionic concentrations useful in ophthalmic irrigation, precipitation is not a problem in freshly prepared solution, long-term storage is proscribed. As insoluble crystals introduced into the eye will cloud vision, the importance of keeping a tissue irrigating solution free of insoluble precipitates may be readily appreciated. A Ringer's solution fortified with sodium bicarbonate and dextrose and injected in an Ocutome® Fragmatome™ instrument deposits pure crystals of calcium bicarbonate in the instrument system. Similar crystals are deposited during surgery inside the eye on the retina, vitreous disk, iris and on exposed uvea or sclera. (Dr. Connor O'Malley, "Salt Contamination of the Eye—An Infusion Hazard". *Ocutome/Fragmatome Newsletter*, 4, No. 4, 1979).

Complicating the maintenance of GBR's stability is the fact that the pH of GBR will gradually increase due to the inadequacy of the bicarbonate-phosphate buffer. To provide proper pH, i.e., about 7.4, the pH must be monitored and adjusted with $CO_2$ immediately prior to use and even during use. The chances for contamination during pH adjustment are great.

A further factor which proscribes long-term storage of GBR is the unavailability of a proper pH at which all of the moieties are stable. Several moieties of GBR are unstable at the physiological pH of about 7.4. Below a pH of about 8, bicarbonate generally decomposes to $CO_2$, resulting both in a loss of bicarbonate concentration and increased pH. On the other hand, glucose stability requires a pH of less than about 6. Glutathione, while biologically effective either in reduced or oxidized form, is preferred in the oxidized form because the reduced form quickly oxidizes in aqueous solutions, preventing proper labeling of the irrigating solution. Oxidized glutathione (glutathione disulfide) is unstable over extended periods of time at a pH of above about 5. The concentration of glutathione may also decrease to an unacceptable concentration when stored over long periods of time in admixture with all other components. Because of the demonstrated efficacy of GBR as an ocular irrigating solution, it would be desirable to provide a formulation which contains the essential factors found in GBR and which may be stored in a sterilized form for use in eye surgery.

Accordingly, it is a primary object of the invention to provide a stable sterile ophthalmic irrigating solution which, in addition to correct electrolyte balance, provides factors necessary for continued metabolism in the endothelial cells, maintenance of the fluid transport pump system, and consequential maintenance of proper corneal thickness and clarity.

Neurosurgery is another important area where there is a need for irrigating solutions which better stabilize irreplaceable tissue. It is well known that destroyed nerve cells, for the most part, are not regenerated. Normal saline is the traditional wound irrigating solution used in neurosurgery, at least partially because of its low cost and ready availability. However, the use of saline has several theoretical disadvantages which may be of unrecognized clinical importance. The pH of saline ranges from 5–7 and is unbuffered; therefore, it causes an acid environment. In the absence of circulating cerebrospinal fluid, as is usually the case in open neurosurgical procedures, this acid pH may cause damage to the exposed brain and spinal cord.

It is another primary object of the present invention to provide an irrigating solution that stabilizes neuro tissue and other sensitive tissues.

SUMMARY OF THE INVENTION

Two separately prepared solutions are provided that when mixed together provide an irrigating solution which has important benefits for irrigating tissue during surgery, particularly irreplaceable tissue such as ocular tissue or neuro tissue. One of the solutions is basic and contains bicarbonate ions and preferably phosphate ions. The other solution is acidic and contains calcium and magnesium ions. Dextrose is provided in one of the solutions, preferably the acidic solution. Glutathione is provided in one of the solutions, preferably the acidic solution. Sodium potassium and chloride ions are each provided in at least one of the solutions. Also provided is gamma-amino butyric acid (GABA), or functional analogues thereof, such as, diamino butyric acid (DABA), which may be used along. The mixed irrigating solution is sufficiently stable for surgical use within about 24 hours of preparation but unstable for long-term use. The segregation of the components into the two partial solutions, which are each stable for extended periods of time, overcomes the inherent long-term stability problem of the irrigating solution. The term "functional analogue" of gamma-amino butyric acid means all structurally related compounds which function to enhance or maintain the corneal endothelial pump. One such preferred functional analogue is (L)diamino-2,4-butyric acid. Certain mixtures of gamma-amino butyric acid and (L)diamino-2,4-butyric acid are especially preferred. Typically, such (L)diamino-2,4-butyric acid is taken as its dihydrochloride.

DETAILED DESCRIPTION OF THE PREFERRED EMBODIMENTS

The present invention is directed generally to a two-part solution system which includes a basic solution and an acidic solution. The composition and concentration of the two solutions are such that they are individually stable and may be separately stored for long periods. When mixed together the two solutions form a tissue irrigating solution that may be used for surgery during the next 24 hours. The mixed solution is useful for ocular surgery as it contains the necessary factors to maintain endothelial cell, integrity and corneal thickness during ocular surgery. It is further found that the same factors are important in maintaining the stability of other sensitive tissues, including nerve tissue. The combined irrigating solution contains the necessary ions for tissue stability, $Ca^{++}$, $Mg^{++}$, $Na^+$, $K^+$ and $Cl^-$ in a bicarbonate-phosphate buffer as well as oxidized glutathione and dextrose. As used herein, "glutathione" is used to refer to either the oxidized form of glutathione (GSSG) or the reduced form (GSH). Irrespective of the form used to prepare the solution, the glutathione will be in its oxidized form in the final mixed solution to avoid confusion in labeling, and the solutions will generally be prepared with oxidized glutathione. The solution may also contain adenosine.

The electrolytes are provided in proportions conducive to cellular integrity and continued cell metabolism. Preferably the proportions of electrolytes resemble BSS, a solution particularly formulated for ophthalmic irrigation rather than Ringer's solution, which was formulated for injection into the cardiovascular system. Preferably the irrigating solution is more substantially buffered than GBR so that the pH does not continually change as does the pH of GBR. However, it is intended that the scope of the present invention be limited only to proportions of electrolytes compatible with body tissues.

The irrigating solution contains from about 130 to about 180 mM/l $Na^+$, from about 3 to about 10 mM/l $K^+$, from about 1 to about 5 mM/l $Ca^{++}$, from about 0.5 to about 4 mM/l $Mg^{++}$, and from about 130 to about 210 mM/l $Cl^-$. To maintain osmotic stability of the cells, the osmolality is between about 250 and about 350 mOsm and preferably about 290–320 mOsm. So as to closely match the physiological pH of 7.4, the pH of the final irrigating solution is between about 6.8 and about 8.0 and preferably about 7.2–7.8. To maintain the fluid pump system, the bicarbonate concentration in the combined irrigating solution is between about 10 and about 50 mM/l. To stabilize the pH, an additional buffering agent is provided. Preferably the buffering agent is phosphate which is provided in sufficient quantity so that final phosphate concentration of the irrigating solution is between about 1 and about 5 mM/l. The final irrigating solution contains between about 2 and about 10 mM/l glucose and between 0.03 and about 0.5 mM/l of oxidized glutathione or the equivalent amount of reduced glutathione. One mole of oxidized glutathione is the equivalent of two moles of reduced glutathione.

The basic solution provides the phosphate and bicarbonate buffering moieties, preferably in the form of dibasic sodium phosphate and sodium bicarbonate. The pH of the basic solution is adjusted to about the physiological pH, of 7.4, preferably to between about 7.2 and about 7.8. As hereinbefore mentioned, the pH of a bicarbonate-containing solution is preferably above about 8.0 to prevent decomposition of the bicarbonate. It has been found, however, that the bicarbonate may be stabilized if it is added to a solution with a pH of above about 8 and thereafter adjusted to a pH between 7 and 8. Accordingly, when the basic solution is prepared, $Na_2HPO_4$ is added prior to the addition of $NaHCO_3$ so that $NaHCO_3$ is dissolved in a solution with a pH of between about 8 and about 9. The solution is thereafter adjusted with dilute acid, such as $H_2SO_4$, $H_3PO_4$ or HCl, to the desired final pH of the basic solution. Alternatively, carbon dioxide may be added to adjust the pH.

Potassium and additional sodium are provided in the basic solution in the form of sodium and potassium salts, such as sodium or potassium chlorides, sulfates, acetates, citrates, lactates, and gluconates. The sodium and potassium are compatible with all of the moieties present in the finished tissue irrigating solution, and sodium chloride and potassium chloride may be added to either solution or divided between the solutions. However, in view of the fact that the basic solution provides the buffer system, the pH of the final irrigation solution may be more accurately determined if all compatible salts are included in the basic solution.

The acidic solution provides the $Ca^{++}$ in the form of calcium chloride, the $Mg^{++}$ in the form of magnesium chloride, the glutathione and the dextrose. The pH is adjusted to below about 5 to provide long-term stability to the dextrose and oxidized glutathione.

The gamma-amino butyric acid (GABA) component may reside in either solution. Typically, GABA, or its functional equivalent, is present at a final concentration of from 0.001 to 1.0 mM/L. A particularly preferred analogue of GABA for this purpose is (L)diamino-2,4-butyric acid. The concentration range of the GABA, or summation of GABA-like components, is typically $10^{-6}$ to $10^{-4}$ moles/liter (0.001 to 0.1 mM/L). A particularly preferred combination involves GABA and (L) diamino-2,4-butyric acid in the molar ratio range of 0.5–1.5:5–9, respectively. For example, an especially preferred combination comprises 0.5 to $1.5 \times 10^{-5}$ moles/L GABA and 6.0 to $10.0 \times 10^{-5}$ moles/L (L)diamino-2,4-butyric acid; wherein said concentrations are relative to the final, combined irrigating solution.

Because of the requirement that the acidic solution have a low pH, it is preferable that the volume of the basic solution greatly exceed the volume of the acidic solution and that the acidic solution contain no buffering agents. The acidic solution may be adjusted below a pH of about 5 with a relatively small amount of HCl. Because the acidic solution is unbuffered, its pH is a reflection of the acid concentration and less acid is needed to adjust the pH of a small volume. The large volume of buffered basic solution may be adjusted very close to the final pH of the irrigating solution and will be relatively unaffected by the addition of the small volume of the acidic solution. Preferably, the ratio of the basic solution volume to the acidic solution volume is about 10 to 1 to about 40 to 1.

The basic solution and the acidic solution are sterilized and separately bottled or contained under sterile conditions by standard techniques, such as autoclaving, or use of sterilizing filters, but preferably by heat sterilization. Typically, the basic solution, which preferably contains only inorganic moieties, is autoclaved, whereas the acidic solution, which preferably contains the organic components, is microfiltered. To avoid the need for measuring volumes in the hospital which may introduce possible error and/or contamination, it is highly preferred that particular volumes of the basic and acidic solutions be bottled so that adding the entire content of a container of the acidic solution to the entire content of a container of the basic solution results in the correctly formulated tissue irrigating solution. The solutions may be mixed up to 24 hours before a surgical procedure without the occurrence of significant pH change and without the formation of detectable precipitates and without degradation.

Precautions to maintain sterility of the solutions and to insure correct mixing of the acidic and basic solutions cannot be overdone. While the manufacturer may take all due precautions to maintain quality control, carelessness by a technician may render all such precautions for naught. Any opening of a container, no matter how carefully performed, increases the likelihood of contamination in the contents. As one method of substantially eliminating the possibility of improper mixing and to reduce the likelihood of contamination, the solutions may be shipped in a container having a first chamber for the basic solution, an isolated second chamber for the acidic solution and means to communicate the chambers without opening the container. The use of such containers are known for the shipment of multi-part medical solutions. As one example, a container may have a lower chamber containing a measured volume of the basic solution separated by a membrane from an upper chamber containing a measured volume of the acidic solution. The container cap may include a plunger means which, when depressed, causes a sharp point or blade depending therefrom to break the membrane. The container is thereafter agitated, as by shaking, to complete the sterile mixing in proper volume of the acidic and basic solutions.

The proper mixing of the acidic and basic solutions may also be carried out by aseptically removing the acidic solution from its package with a sterile syringe and needle and aseptically adding the acidic solution to the contents of the basic solution package through the rubber stopper. Alternately, a sterile double-ended needle can be used to transfer the acidic solution to the basic solution by aseptically inserting one end of the needle into the vial containing the acidic solution and then aseptically inserting the other end of the needle into the basic solution package, whereby the vacuum that is maintained therein transfers the acidic solution to the basic solution and is mixed.

The two-part solution of the present invention also provides an advantage as to safety if a technician should fail to properly mix the two solutions. The larger volume basic solution is physiologic so that there is less chance of toxicity if the basic solution were used without the acidic solution being mixed therewith.

The manner of providing an irrigating solution which is sterile and storable, and which provides the correct electrolyte balance as well as factors necessary for cell metabolism may now be fully appreciated. By segregating the phosphate and bicarbonate ions from the divalent magnesium and calcium ions, the buildup of insoluble precipitates is eliminated. The solution that contains the bicarbonate is slightly basic and the bicarbonate therein is stabilized as a result of initially dissolving the bicarbonate at a sufficiently basic pH. The other solution is sufficiently acidic to stabilize dextrose and oxidized glutathione. The basic and acidic sterile solutions are simply combined to provide the correctly formulated irrigating solution without adding further substances, adjusting the pH or introducing apparatus, any of which are potentially contaminating. While the final combined irrigating solution is not stable for an extended period of time, it is stable for sufficiently long periods, i.e., 24 hours, so that the irrigating solution may be carefully mixed under unhurried conditions prior to an operation and remain stable throughout the operation. The buffer system is adequate to maintain a generally constant pH for at least a 24-hour period, eliminating the need to monitor or adjust the pH.

EXAMPLE 1

Separate sterile basic and acidic solutions were made and packaged. A sample of the basic solution and a sample of the acidic solution were mixed, and the combined solution was tested for stability as well as the ability of maintaining the structural integrity and function of rabbit and human endothelia during in vitro perfusion, i.e., simulating intraocular irrigation.

Part I (basic solution) was made by dissolving 2.582 Kg sodium chloride, 138.2 grams potassium chloride, and 151.55 grams anhydrous dibasic sodium phosphate in water for injection at about 20° C. Then 918.75 grams of sodium bicarbonate where added and dissolved. Additional water for injection was added to make about 350 Kg batch weight and 1N HCl added (about 1 liter) to adjust pH to about 7.4. The solution was then passed through a 0.45 micron Millipore filter and each bottle (USP Type I glass) was filled with about 480 ml of solution. The filled bottles were then stoppered, vacuumed and sealed. The sealed bottles were sterilized by autoclaving at 121° C. for about 23 minutes.

Part II (acidic solution) was made by dissolving 385 grams calcium chloride dihydrate, 500 grams magnesium chloride hexahydrate, 2300 grams dextrose, and 516 grams of 94% oxidized glutathione glutathione disulfide) in water for injection to make a final batch volume of about 100 liters. The solution was then sterile filtered through a 0.22 micron membrane filter and aseptically filled into presterilized 20 ml Type I glass vials and sealed with presterilized rubber stoppers. (Alternately, the solution can be packaged in Type I glass ampules.)

After adding 20 ml of Part II (acidic solution) to a 480 ml bottle of Part I (basic solution) and mixing, in vitro corneal endothelial perfusion studies were carried out on both rabbit and human donor corneas along with commercial lactated Ringer's solution and Plasmalyte 148 (pH 7.4) for comparison. Corneas from rabbits and human donor corneas were excised and mounted in a dual chambered specular microscope. A swelling rate ($\mu$/hr) was calculated by regression analysis from measurements of sequential changes in corneal thickness. Isolated corneas were perfused at 37° C. at 15 mm Hg with each of the test solutions for up to three hours. Each experiment was studied as a pair, one cornea receiving the tissue irrigating solution of the instant invention and the other cornea perfused with either lactated Ringer's solution or Plasma lyte. The corneal epithelium in all rabbit experiments was intact and covered with medical grade silicone oil. In the human corneas, the epithelium was debrided prior to mounting in the specular microscope. At various times during the course of the perfusion, the corneas were fixed for scanning and transmission electron microscopy in 2.7% glutaraldehyde and phosphate buffer (pH 7.2, 330 mOsm) for at least eight hours at 4° C. They were then post fixed in 2% osmium tetroxide for one hour and embedded in a low viscosity epoxy medium. For scanning electron microscopy (SEM), the resin was washed off the endothelial surface of a portion of each cornea according to the modified method of Cleveland and Schneider, "A Simple Method Preserving Ocular Tissue for SEM," *Vision Research* 9, pp. 1401-1402, 1969. After polymerization of the tissue specimens overnight at 37° C. and for 48 hours at 60° C., the tissue was glued to SEM specimen stubs coated rotationally with carbon and gold palladium metal and viewed with an AMR (1000) scanning electron microscope. Endothelial perfusion of tissue irrigating solution of the instant invention to the rabbit cornea resulted in a swelling rate of 0.001 μ/hr. On ultrastructural examination, the endothelial cells of all corneas were intact with normal cell morphology maintained throughout the three-hour period.

In the paired corneas, the endothelium was perfused with Plasmalyte 148 (ph 7.4). There was marked corneal swelling at a rate of 84.5 N/hr. Upon ultrastructural examination with SEM, the endothelial cells appeared to be separating at the junctions between cells, and on transmission EM, the cells were balled up and the junctions broken. In some corneas that were perfused with Plasmalyte, complete junctional breakdown occurred and the endothelial cells balled upon Descemet's membrane.

The paired corneas that were perfused with lactated Ringer's solution had a swelling rate of 32.7 μ/hr. On ultrastructural examination, the cells were morphologically swollen and there appeared to be breaks in the outer plasma membrane. Cytoplasmic bleeding was apparent on the outer surface of the corneal endothelial cells and on transmission electron microscopy there was dilation of the endoplasmic reticulum, condensation of the mitochondria and microfilament network along the outer plasma membrane. Associated with the cytoplastic changes, there was also edema of the endothelial cells adjacent to Descemet's membrane.

Endothelial perfusion of human corneas with tissue irrigating solution of the instant invention had a negative swelling rate of 24.6 μ/hr. and, upon ultrastructural examination, the endothelial cells were shown to be intact, the junctions intact, and the cell organelles normal by transmission electron microscopy. The paired corneas that were perfused with Plasmalyte all showed junctional breakdown between the individual cells and balling of the endothelial cell. These ultrastructural changes were associated with a corneal swelling of 19 μ/hr.

By comparison, the paired corneas that were perfused with lactated Ringer's solution showed a slight deswelling of only −5 μ/hr. but there were associated ultrastructural changes in the surface morphology of the corneas of older humans. Junctional breakdown was apparent, and balling of the cells and nucleus with marked vacules in the cytoplasm occurred. However, the cell organelles within the endothelium appeared normal.

The data obtained in this study indicates that Plasmalyte 148, an IV electrolyte solution used for phacoemulsification, caused corneal endothelial cell breakdowns and functional disruption of the endothelium during in vitro perfusion and therefore may cause corneal edema after phacoemulsification. The data obtained also indicates that the tissue irrigating solution of the instant invention maintains human and rabbit corneal function and ultrastructural integrity for a three-hour period.

By comparison, lactated Ringer's solution is only able to maintain the corneal endothelial cell integrity and ultrastructural appearance to variable degrees both in rabbits and in humans and may be adequate for short-term irrigation of the cornea, but will provide, at the very best, minimal protection to the corneal endothelium when perfused to the endothelium for extended periods of time.

EXAMPLE 2

The effects of continuous irrigation with the tissue irrigating solution and with 0.9% saline on the cerebral cortex of the cat has been compared. Tissue irrigating solution in accordance with the present invention was freshly mixed as per Example 1. The composition of the tissue irrigating solution is compared with isotonic saline and cerebrospinal fluid in Table 1 below:

TABLE 1

| | Cerebrospinal fluid meq/L* | Irrigating Solution meq/L** | 0.9% normal saline meq/L |
|---|---|---|---|
| $Na^+$ | 145.0 | 150.7 | 154 |
| $K^+$ | 3.0 | 5.1 | 0 |
| $Mg^{++}$ | 2.2 | 2.0 | 0 |
| $Ca^{++}$ | 2.3 | 2.1 | 0 |
| $H_2PO_4^-$ | 1.0 | 3.5 | 0 |
| $Cl^-$ | 125.0 | 131.4 | 154 |
| $HCO_3^-$ | 24.0 | 25.0 | 0 |
| pH | 7.35 ± .1 | 7.2 ± .4 | 6.0 ± 1.0 |
| Osmolality | 306 ± 10 | 305 ± 15 | 290 |

*Diem et al., Documenta Geigy Scientific ta Switzerland: Ciba-Geigy Limited, 1972, p. 523.
**Irrigating Solution also contains 2 non-ionic components: 5.1 mmol dextrose and 0.28 mmol oxidized glutathione The subjects were six adult mongrel cats. The animals were anesthetized with Surital ® and atropine and were maintained on animal ventilators. Intravenous and intra-arterial catheters were placed via a femoral cut-down. Blood pressure, temperature, and arterial blood gases were monitored. Bilateral craniectomies were performed and the dura and arachnoid elevated from the cortex using microsurgical technique. Three in-line platinum disc electrodes were placed laterally on the exposed cortex to measure evoked potentials, which were recorded on a Clinical Technology Corporation Model 2000 averaging computer. pH was monitored bilaterally using Microelectrodes Inc., pH electrodes number 408C and standard Beckman pH meters. Local cerebral blood flow was monitored using hydrogen clearance methods, which have been described elsewhere. C. Myklebust et al., *IEEE Trans BME* 28(3): 265-267 (1981).

Immediately following exposure of the cortical surface, continuous drip irrigation was initiated using small bore needles at a rate of 15 cc/hr, to saturate the cortical surface. 0.9% saline was used on one side and the irrigating solution on the other for a minimum of 4 hours in each animal.

Surface pH, evoked potentials and local cerebral blood flow were measured at regular intervals throughout the trials. In four animals, shortly prior to termination of the trial, Evan's blue dye was injected intravenously and the cortical surface examined under magnification for evidence of extravasation, indicating blood-brain barrier injury.

In two animals, after the minimum 4 hour recording period, the animals were allowed to become hypoxic for a 5 minute period of time in order to evaluate the additional factors of anoxia and/or ischemia on the parameters measured. These parameters were recorded at very short intervals for 3 hours following the episode.

Changes in surface pH as a function of time are depicted in Table 2 below:

TABLE 2

| Hrs. | pH Saline | pH Irrigating Solution |
| --- | --- | --- |
| 0 | 7.4 | 7.3 |
| ½ | 7.4 | 7.2 |
| 1 | 7.4 | 7.1 |
| 1½ | 7.3 | 7.3 |
| 2 | 7.2 | 7.2 |
| 2½ | 6.9 | 7.3 |
| 3 | 6.8 | 7.3 |
| 3½ | 6.8 | 7.3 |
| 4 | 6.6 | 7.3 |

Marked depression in pH was seen at 1½ to 2½ hours with saline irrigation. Changes in pH related to saline irrigations became statistically significant at approximately 2 hours (F=2.9). This had increased markedly at the 4 hour termination point, (F=21.3). No significant changes in pH were seen with the tissue irrigating solution. The pH differences between normal saline and the irrigating solution became significant at the 2½ hour point (F=4.59) and had more than doubled by termination of the trial (F=11.2).

In the trials with induced hypoxia, decreases in pH were seen at both sides but were more marked on the saline irrigated surface. These changes resolved over the three-hour measurement period at the irrigating solution surface; on the saline side, the pH continued to decrease. Gross brain swelling occurred bilaterally along with the post-hypoxia pH changes; this resolved coinciding with the pH changes on the irrigating solution surface, but remained unchanged on the saline side.

Blood-brain barrier changes were prominent in 3 of the 4 animals injected with Evans blue dye. There was no dye extravasation on the irrigating solution surfaces, except in one animal with a small pial tear. Changes were marked on the saline sides, with multiple areas of breakdown in two, and confluent dye extravasation in the third.

These findings tend to substantiate that the irrigating solution represents an improvement for neurosurgical procedures, primarily because it is buffered with $HCO_3$ and contains glucose and glutathione. The pH changes observed with normal saline were dramatic; while the extent of injury to the nervous system produced is difficult to assess, its existence certainly can be strongly suspected. In addition to dysfunction of enzyme activity and alteration of electrical potentials causing abnormalities of conduction, it is conceivable that secondary ionic shifts might occur at the neuronal level. Swiontek et al., *Surg Neurol* 14: 365-369, (1980) have suggested that severe pH changes often represent secondary manifestations of nervous tissue injury.

The changes in the blood-brain barrier were also prominent. It has been observed that the blood-brain barrier is maintained by the endothelial tight junctions; these in turn, are maintained by ionic charges. Several investigators have emphasized that the production of cerebral edema is related to the breakdown of the blood-brain barrier with gaps occurring at the level of the tight junction related to increased permeability. The lack of changes in the blood-brain barrier status may be related to preservation of the endothelial tight junction by the calcium bicarbonate buffer present in the irrigating solution.

Of particular interest were the subjects in which short periods of hypoxia were induced. In both instances, marked pH decreases were seen immediately following the episode. These persisted and became worse on the surfaces irrigated with normal saline. However, on the BSS Plus side, recovery of the pH almost to baseline, was seen in both animals. Additionally, the edematous changes which were seen shortly after the hypoxic episode resolved on the irrigating solution irrigated cortex. While it is impossible to establish a mechanism on the basis of these two trials perhaps reestablishment of the endothelial tight junctions assisted in the resolution of the edema. In one of these two trials, the blood-brain barrier changes were particularly prominent on the normal saline side, with a confluent field of disruption.

These results show that the irrigating solution of the invention represents an improved irrigating solution for neurosurgical procedures.

The usefulness of the two-part tissue irrigating solution has been illustrated by way of example with reference to two very critical types of tissues, ocular tissue and neuro tissue. However, the components of the irrigating solution which are important in stabilizing these tissues are important in stabilizing other tissues, and the desirability of having such a solution without the need to prepare it extemporaneously apply to other surgical applications as well. Examples of where the irrigating solution is useful include irrigating vessels in microvascular surgery and in organ transplants; graft sites in burn-graft procedure; joint space in any major orthopedic procedure, e.g., hip or knee replacement, ear canal during ear, nose and throat surgery, the pulmonary tree in bronchoscopy procedures, the peritoneal cavity during abdominal surgery, heart chambers during open heart surgery, saphenous veins during coronary artery by-pass surgery, the uterus in gynocology surgery, e.g., a D & C, and the bilary tree or pancreatic drainage ducts in pancreatobiliary surgery. This list is by no means exhaustive and is not intended to limit the present invention.

While the whole invention has been described in terms of preferred embodiments, modifications obvious to one skilled in the art may be without departing from the scope of the present invention which is limited only by the following claims:

What is claimed is:

1. An article of manufacture containing a two-part tissue irrigating solution comprising:
    (a) a package containing a stable, sterile basic solution containing bicarbonate ions, said package containing the solution under vacuum;
    (b) a vial containing a stable, sterile acidic solution containing calcium ions, magnesium ions, dextrose, and glutathione, said vial being closed with a rubber stopper;
    (c) a sterile double-ended needle; at least one of said solutions containing sodium ions, at least one of said solutions containing potassium ions, at least one of said solutions containing chloride ions, and at least one of said solutions containing gamma-amino butyric acid, (L)diamino-2,4-butyric acid, or a mixture of gamma-amino butyric acid and (L)diamino-2,4-butyric acid,
    said acidic and basic solutions being mixed together by aseptically inserting one end of the double-ended needle into the package containing the basic solution, and the other end into the vial containing the acidic solution, and transferring the acidic solution into the basic solution by the vacuum under which the basic solution is maintained, said acidic and basic solutions when mixed together forming the irrigating solution for irrigating body tissues during surgery, the irrigating solution containing between about 130 and about 180 mM/l sodium ions, between about 3 and about 10 mM/l potassium ions, between about 1 and about 5 mM/l calcium ions, between about 0.5 and about 4 mM/l magnesium ions, between about 10 and about 50 mM/l bicarbonate ions, between about 2 and about 10 mM/l dextrose, between about 0.03 and about 0.5 mM/l oxidized glutathione or the equivalent amount of reduced glutathione, and between about 0.001 and about 1.0 mM/L gamma-amino butyric acid, (L)diamino-2,4-butyric acid, or mixtures thereof, and said irrigating solution having a pH of between about 6.8 and about 8.0 and an osmolality of between 250 and about 350 mOsm/kg.

2. An article of manufacture according to claim 1 wherein said sodium ions and said potassium ions are contained in said basic solution, and said basic solution also contains phosphate ions in sufficient quantity that the phosphate ion concentration in said tissue irrigating solution is between about 1 and about 5 mM/l.

3. A method of maintaining tissue stability during surgery which comprises mixing a basic partial solution containing bicarbonate ions and an acidic partial solution containing calcium ions, magnesium ions, dextrose, and glutathione, at least one of said partial solutions containing potassium ions, at least one of said partial solutions containing chloride ions, at least one of said partial solutions containing sodium ions, and at least one of said partial solutions containing gamma-amino butyric acid, (L)diamino-2,4-butyric acid, or a mixture of gamma-amino butyric acid and (L)diamino-2,4-butyric acid, to form a combined solution, said combined solution containing between about 130 and about 180 mM/l sodium ions, between about 3 and about 10 mM/l potassium ions, between about 1 and about 5 mM/l calcium ions, between about 0.5 and about 4 mM/l magnesium ions, between about 10 and about 50 mM/l bicarbonate ions, between about 2 and about 10 mM/l dextrose, between about 0.03 and about 0.5 mM/l oxidized glutathione or the equivalent amount of reduced glutathione, and between about 0.001 and about 1.0 mM/L gamma-amino butyric acid, (L)diamino-2,4-butyric acid, or mixtures thereof, said solution having a pH of between about 6.8 and about 8.0 and an osmolality of between 250 and about 350 mOsm/kg. and irrigating the tissue with said combined solution.

4. A method according to claim 3 wherein said sodium ions are contained in said basic solution.

5. A method according to claim 3 wherein said potassium ions are contained in said basic solution.

6. A method according to claim 3 wherein the combined solution has an osmolality of between about 290 and about 320 mOsm/kg.

7. A method according to claim 3 wherein the combined solution has a pH of between about 7.2 and about 7.8.

8. A method according to claim 3 wherein phosphate ions are contained in said basic partial solution in sufficient quantity so that the phosphate ion concentration in said combined solution is between about 1 and about 5 mM/l.

9. A method according to claim 8 wherein the pH of said basic solution is between about 7.2 and about 7.8, and the pH of said acidic solution is below about 5.

10. A method according to claim 8 wherein the volume ratio of said basic solution to said acidic solution is between about 10:1 and about 40:1.

11. A method according to claim 8 wherein said sodium ions are contained in said basic solution.

12. A method according to claim 8 wherein said potassium ions are contained in said basic solution.

13. A method according to claim 8 wherein said basic solution contains sodium chloride, potassium chloride, dibasic sodium phosphate, and sodium bicarbonate, and said acidic solution contains calcium chloride, magnesium chloride, dextrose, and oxidized glutathione.

14. A method according to claim 13 wherein the pH of said basic solution is between about 7.2 and about 7.8.

15. A method according to claim 13 wherein the pH of said acidic solution is below about 5.

16. A method according to claim 13 wherein the volume ratio of said basic solution to said acidic solution is between about 10:1 and about 40:1.

* * * * *